United States Patent
Berg

Patent Number: 5,603,705
Date of Patent: Feb. 18, 1997

[54] CATHETER JOINT WITH RESTRAINING DEVICE

[75] Inventor: Todd A. Berg, Lino Lakes, Minn.

[73] Assignee: SciMed Life Systems, Inc., Maple Grove, Minn.

[21] Appl. No.: 441,260

[22] Filed: May 15, 1995

Related U.S. Application Data

[63] Continuation of Ser. No. 171,925, Dec. 22, 1993, abandoned.

[51] Int. Cl.⁶ ................................. A61M 25/00
[52] U.S. Cl. ................................. 604/282
[58] Field of Search .................... 604/282, 280, 604/283

[56] References Cited

U.S. PATENT DOCUMENTS

| | | | |
|---|---|---|---|
| 3,485,234 | 12/1969 | Stevens | 604/282 |
| 4,210,478 | 7/1980 | Shoney | 156/242 |
| 4,419,095 | 12/1983 | Nebergall et al. | 604/96 |
| 4,516,970 | 5/1985 | Kaufman et al. | 604/270 |
| 4,531,943 | 7/1985 | Van Tassel et al. | 604/280 |
| 4,588,399 | 5/1986 | Nebergall et al. | 604/280 |
| 4,817,613 | 4/1989 | Jaraczewski | 604/282 |
| 4,842,590 | 6/1989 | Tanabe et al. | 604/282 |
| 4,863,442 | 9/1989 | DeMello et al. | 604/282 |
| 5,017,259 | 5/1991 | Kohsai | 156/294 |
| 5,078,702 | 1/1992 | Pomeranz | 604/280 |
| 5,160,559 | 11/1993 | Scovil et al. | 156/73.6 |
| 5,221,270 | 6/1993 | Parker | 604/282 |
| 5,234,416 | 8/1993 | Macaulay et al. | 604/282 |
| 5,254,107 | 10/1993 | Soltesz | 604/282 |
| 5,279,596 | 1/1994 | Castaneda | 604/282 |

*Primary Examiner*—Todd E. Manahan
*Attorney, Agent, or Firm*—Nawrocki, Rooney & Sivertson, P.A.

[57] ABSTRACT

An intravascular catheter of the type having an inner tubular member defining a lumen, an outer tubular member surrounding said inner member, and a support member mounted between the tubular members to provide rigidity to the flexible catheter. The support member comprises a wire braid, and in the preferred embodiment comprises a stainless steel wire braid which has been tempered or hardened to give it a significantly high tensile strength. This higher tensile strength affords significantly greater kink resistance to the flexible catheter as the lumen size is increased and the wall thickness is decreased, however, the high tensile strength wire braid has the disadvantage of tending to flare out during a bonding process when the catheter is joined to a tip, for example. In this invention, a retaining device is added to the end of the catheter to be joined, for preventing the flaring of the wire braid, whether the wire be of a high tensile strength or not.

9 Claims, 3 Drawing Sheets

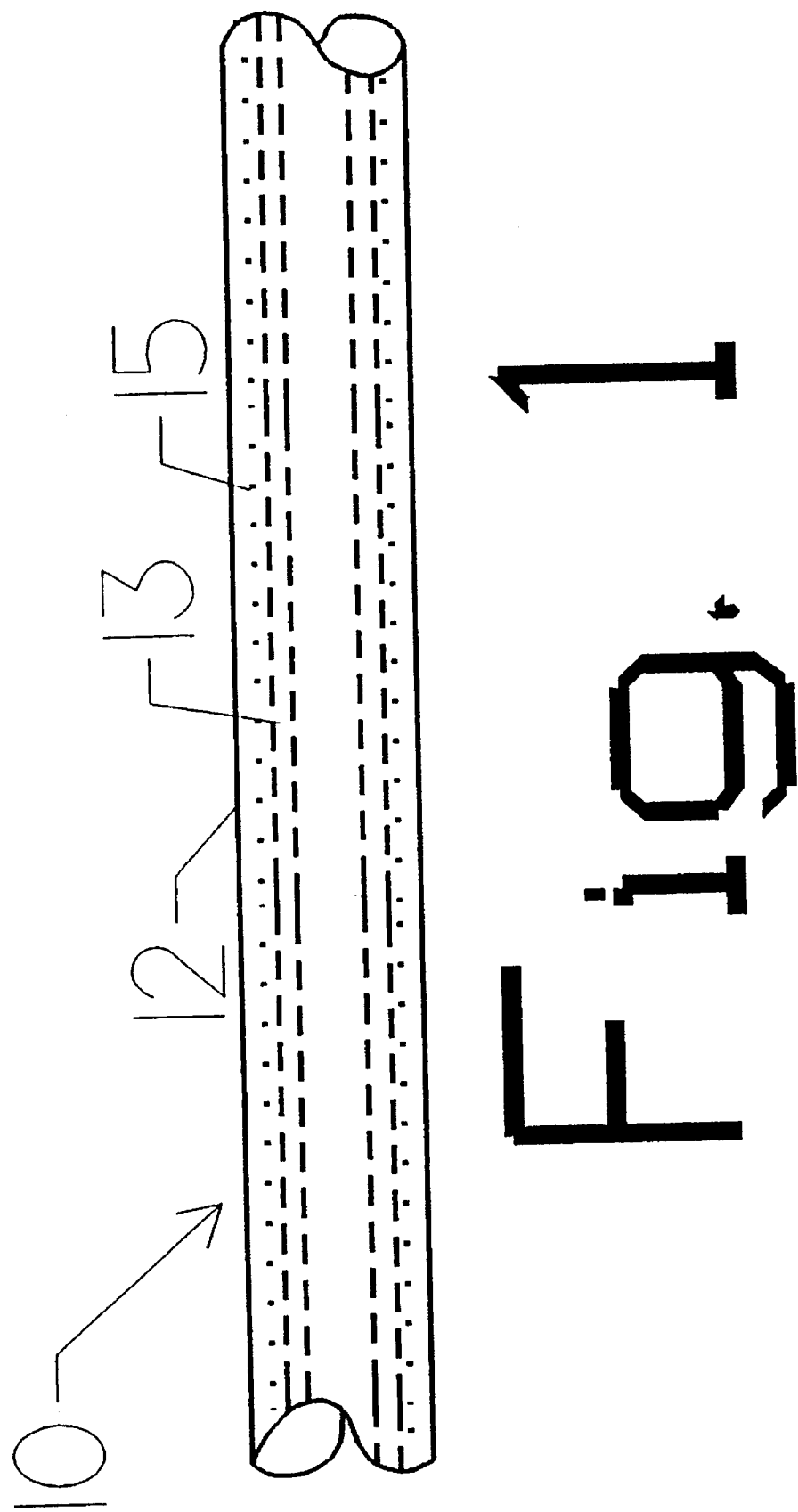

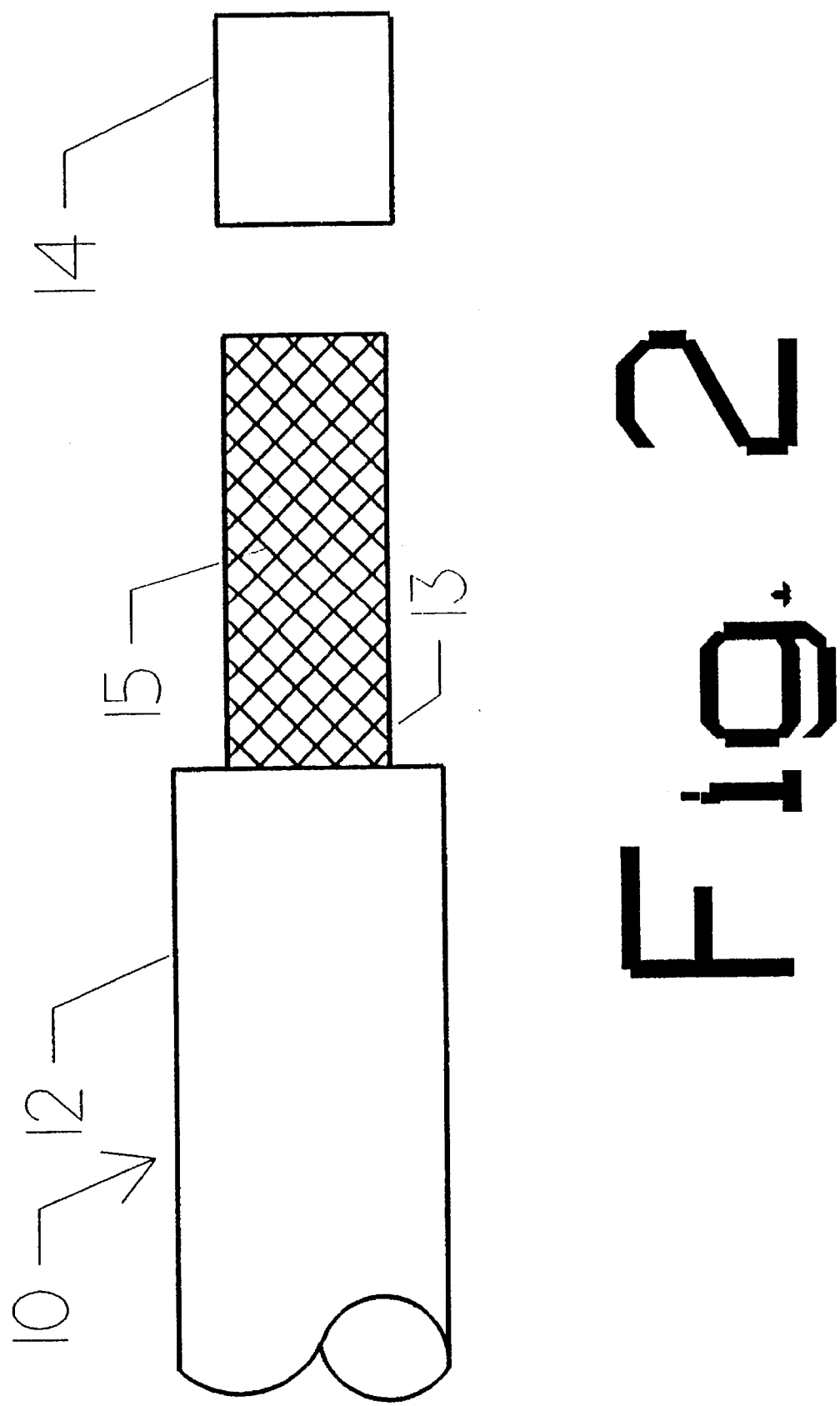

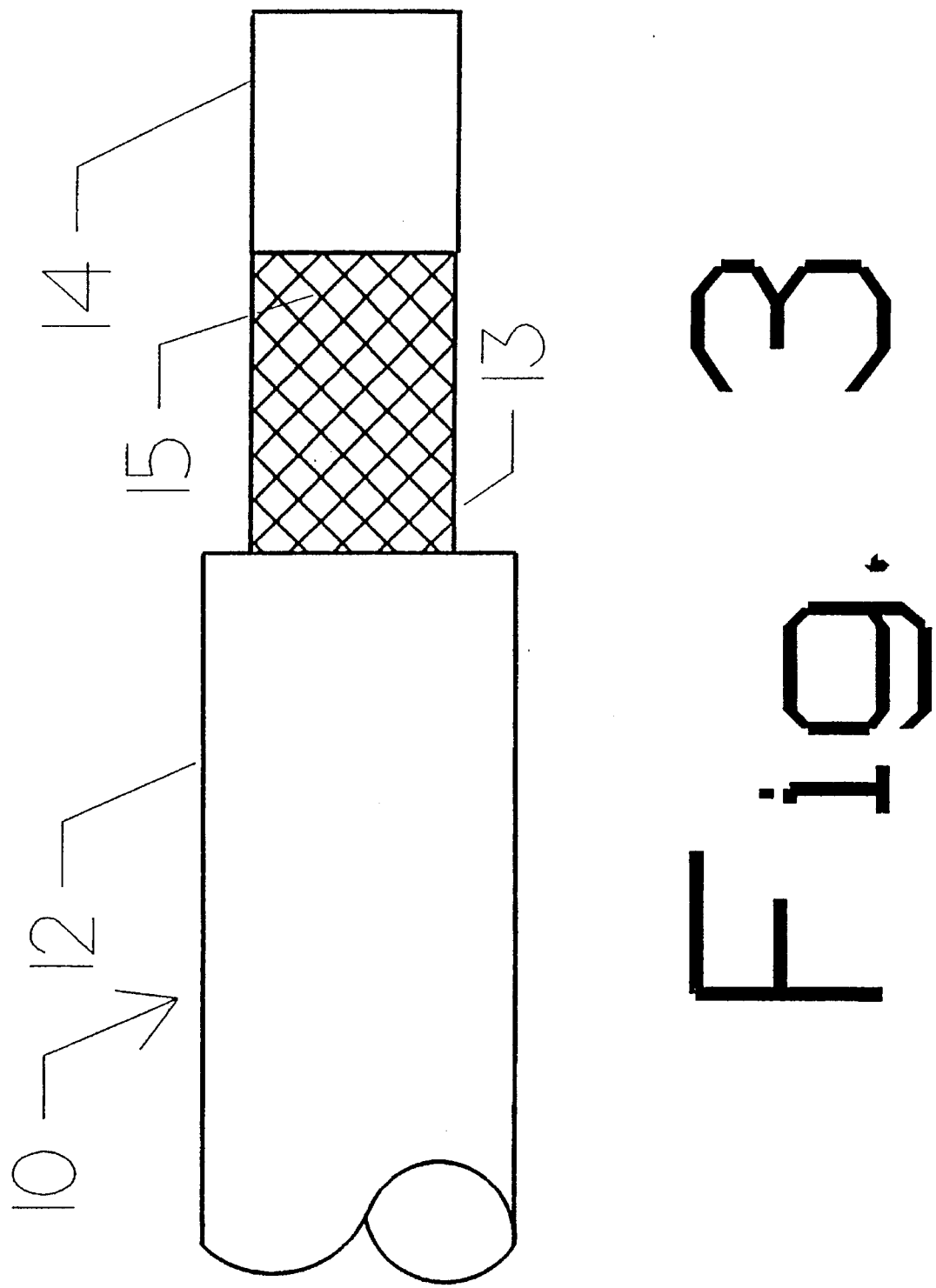

CATHETER JOINT WITH RESTRAINING DEVICE

CROSS REFERENCE TO CO-PENDING APPLICATIONS

This application is a continuation of U.S. patent application Ser. No. 08/171,925, now abandon filed on Dec. 22, 1993, entitled "Catheter Joint With Restraining Device". This application is also related to U.S. patent application Ser. No. 08/108,973, filed Aug. 18, 1993, now abandon entitled "Improved Thin-Walled Catheter".

BACKGROUND OF THE INVENTION

1. Field of the Invention

The present invention generally relates to the field of intravascular medicine and more particularly to the field of catheters such as guide catheters used for the placement of medicines and medical devices within the body.

2. Description of the Prior Art

The use of intravascular catheters for treatment of the body is well known in the field of medicine. The need for a choice of catheter sizes and types has grown rapidly as the techniques for their use have been greatly improved and the types of medical uses have expanded quickly.

Prior art catheters often comprise a pair of congruent tubes, the inner one defining a lumen. A hub is connected at the proximal end of the tubes which in addition to providing access to the lumen for fluids and the like, is often used to provide torques and other necessary pressures to the tubes during their placement within the body. A tip of a selected design is placed at the distal end of the tubes. Flexibility is an essential part of the catheter so that it may be successfully torqued, pushed and pulled on its way through the vascular passage to the desired site in the body. For control of the catheter and to prevent its kinking from excessive flexing a certain amount of rigidity is required. The prior art catheters often meet this need for rigidity by adding a support member between the two tubes. This support member may comprise a braid of metal wire wrapped around the inner tube, and often imbedded within the outer tube.

As specific examples of the type of prior art catheters described above, note U.S. Pat. No. 3,485,234, issued Dec. 23, 1969, to R. C. Stevens, for TUBULAR PRODUCTS AND METHOD OF MAKING SAME; and, European Patent Application, Publication No. 0 277 366/A1, Priority Jun. 1, 1987, by Bruce h. Ward, for GUIDING CATHETER AND METHOD FOR MAKING IT. Each of these references teaches, in general, the prior art type of catheter discussed above.

One problem that has arisen is that as it becomes desirable to increase the diameter of the catheter lumen, it also becomes desirable to decrease the thickness of the walls of the tubes that form the catheter. However, it has been found that in thinner-walled catheters it is more difficult to prevent the kinking of the catheter. This negative effect on flexibility is overcome by the above cited co-pending Application, which is incorporated by reference herein.

The disadvantage of the prior art was overcome by providing a high tensile, stainless steel braid as the support structure. However, it has been found that the use of the high tensile metal braid may cause an additional problem for practitioners of the catheter art. It has been seen that the high tensile wire has a tendency to flare or spring out during the heating process used in joining the catheter to a tip or other apparatus. In a similar way, this flaring and springing of the support braid wire is found in prior art catheters even when using the lower tensile type of wire. This flaring will interfere in the proper joinder of the catheter to, for example, a tip and is clearly undesirable and unacceptable in an intravenous catheter.

SUMMARY OF THE INVENTION

The present invention overcomes the disadvantage described above by providing an improved structure and method for joinder of the catheter to any selected apparatus. In the preferred embodiment at least one end of the catheter, normally the distal end, is ground down by an abrasion tool to provide a length of reduced diameter suitable, in particular, for lap-joint type connection to a tip or other apparatus. A restraining material, preferably a thin-walled heat shrink polyester, is also provided to be placed over at least a portion of the reduced diameter length to prevent flaring of the metal braid during the joinder process.

In the preferred embodiment, the restraining material is in the form of a sleeve having a tubular shape with an inner diameter adapted to allow placement of the sleeve over at least a portion of the reduced diameter length at the end of the catheter; and a length at most equal to the length of the reduced diameter portion of the catheter.

As described, the apparatus and method of this invention provides the advantage of allowing use of the high tensile metal braid by restraining flaring of the metal during heat bonding to a tip or other device, thus improving kink performance in the thin-walled catheters which use the high tensile wire. The invention provides the same restraining advantage for catheters which may not use the high tensile wire, but which have the same flaring problem. This invention also provides the advantage of providing a more durable bond of the catheter to the tip or other apparatus by the increased surface area of the lap type bonding. Finally, the apparatus of this invention offers an additional advantage in the form of a stiffness transition in that the ground or abraded step portion of the bond balances the hardness of the main catheter to the softness of a tip, a balance which is known to provide clinical value.

BRIEF DESCRIPTION OF THE DRAWINGS

Other objects of the present invention and many of the attendant advantages of the present invention will be readily appreciated as they become better understood by reference to the following detailed description when considered in connection with the accompanying drawings, in which like reference numerals designate like parts throughout all figures:

FIG. 1 is a plan view showing a portion of a catheter;

FIG. 2 is another plan view of a portion of the catheter of FIG. 1 with a length of the catheter ground down to a lesser diameter, and showing a sleeve; and FIG. 3 is a plan view of FIG. 2 showing the sleeve after mounting on the ground-down length of the catheter.

DETAILED DESCRIPTION OF THE PREFERRED EMBODIMENT

FIG. 1 shows a guide catheter 10, which may be a thin-walled catheter. Catheter 10 comprises an outer tubular member 12 which surrounds and is coaxial with an inner tubular member 13 shown in dashed phantom lines. A support member 15 is shown in dotted phantom lines.

Member 15 is a braid of metal wire, which may be high tensile wire, that also surrounds and is coaxial with member 13.

FIG. 2 is a drawing of a portion of catheter 10. Member 12 is shown having an end portion ground or abraded away. As shown in FIG. 2, member 12 has been completely ground down to metal braid 15. However, it should be recognized that this invention will also operate fully if only a portion of member 12 is abraded away. FIG. 2 also shows a restraining device 14. Device 14 is shown in the preferred embodiment to be a tubular sleeve. Sleeve 14 is, preferably, a thin-walled heat shrink polyester having a length sized to cover at least a portion of the abraded length of member 12, and an inner diameter sized to allow it to fit over the reduced diameter of the end portion of catheter 10 caused by the abrasion of member 12. In this preferred embodiment, sleeve 14 has a thickness of approximately 0.0005 inches, thus allowing it to be completely imbedded between the reduced diameter portion of catheter 10 and the tip or other device used to complete the lap joint with catheter 10.

FIG. 3 is a plan view of the apparatus of FIG. 2 showing restraining device mounted on the reduced diameter portion of catheter 10. Due to the proper sizing of device or sleeve 14, it has been slid onto and covers at least a portion of the reduced diameter region of catheter 10. Sleeve 14 is seen to fit over enough of the end portion of braid 15 so that, when sleeve 14 is heated, it will shrink to and retain the metal wire strands of braid 15.

It should be recognized that though restraining device 14 is shown and described as a tubular member in this embodiment, other forms could be used as well For example device 14 could be a simple strip of heat shrink polyester adapted to be wrapped around the reduced diameter portion of catheter 10. The important feature is that after it has been heated to encapsulate the end of the wire braid, device 14 restrains the wire from surfacing through any joinder by flaring or springing out.

For the process of forming the apparatus of this invention, an abrasive forming tool is used to remove the material of member 12 from its outside surface for 360 degrees from one end of catheter 10. This forms a straight step from the end which allows the abraded or ground portion of catheter 10 to act as the male portion of a lap joint to coact with a female portion of a soft tip or other device it is desired to connect to the apparatus of this invention. The step is preferably a reduction in wall thickness of approximately 0.002 to 0.006 inches, thus allowing for the use of the 0.0005 inch restraining device 14. The length of the abraded portion of catheter 10 is preferably about 0.125 inches, thus allowing for a significant bonding surface area when used in a lap joint. As used herein, the terms "ground" and "abraded" have the same meaning.

Having thus described the preferred embodiments of the present invention, those of skill in the art will readily appreciate the other useful embodiments within the scope of the attached claims.

I claim:

1. Catheter apparatus having at least outer and inner congruent tubular structures and a support structure mounted between said tubular structures, said support structure comprising a metal braid, the improvement comprising:
   a. a step in the catheter apparatus for reducing the diameter of the catheter apparatus for a predetermined stepped region between the step and one end of the catheter apparatus; and
   b. restraining apparatus having an outer diameter less than the outer diameter of said outer congruent tubular structure mounted on at least a portion of the stepped region, said restraining apparatus and said stepped region defining a male portion wherein said male portion is adapted to be selectively joined in a lap-joint type connection to a further apparatus, wherein said further apparatus covers said restraining apparatus when connected thereto.

2. The apparatus of claim 1 in which the restraining apparatus comprises a sleeve.

3. The apparatus of claim 2 in which the sleeve has a length at most equal to the length of the stepped region.

4. The apparatus of claim 1, 2, or 3 in which the restraining apparatus comprises a heat shrink polyester.

5. The apparatus of claim 1, 2, or 3 in which the restraining apparatus comprises a thin-walled heat shrink polyester having a thickness of approximately 0.0005 inches.

6. The apparatus of claim 1, 2, or 3 in which the metal braid comprises high tensile stainless steel.

7. Catheter apparatus having at least outer and inner congruent tubular structures and a support structure mounted between said tubular structures, said support structure comprising a metal braid, the method of making an improved joinder apparatus comprising the steps of:
   a. reducing the diameter of the catheter apparatus for a predetermined length at least at one end of the catheter apparatus, and
   b. mounting a support structure restraining device having an outer diameter less than the outer diameter of said outer congruent tubular structure on at least a portion of the reduced diameter length, said support structure restraining device and said reduced diameter length defining a male portion wherein said male portion is adapted to be selectively joined in a lap-joint type connection to a further apparatus with said further apparatus covering said support structure restraining apparatus.

8. The method of claim 7 in which the step of reducing the catheter apparatus for a predetermined length includes abrading the catheter apparatus to form a step down to a reduced diameter at least equal to the diameter of the support structure.

9. The method of claim 7 or 8 in which the mounting step includes mounting a tubular sleeve on at least a portion of the reduced diameter length.

* * * * *